United States Patent [19]

Taboga

[11] 4,262,633
[45] Apr. 21, 1981

[54] MEANS AND METHODS OF RECLAIMING AND PROCESSING BIODEGRADABLE WASTE INTO POULTRY PRODUCTS AND HUMUS-LIKE SUBSTANCES

[76] Inventor: Leandro Taboga, 9360 Senate Dr. #2B, Des Plaines, Ill. 60016

[21] Appl. No.: 36,790

[22] Filed: May 7, 1979

[51] Int. Cl.³ .............................................. A01K 67/00
[52] U.S. Cl. ...................................... 119/1; 119/51 R
[58] Field of Search .................... 210/2, 14, 17, 59; 119/1, 15, 51 R

[56] References Cited

U.S. PATENT DOCUMENTS

| | | |
|---|---|---|
| 2,867,055 | 1/1959 | Lebiedzinski ........................ 119/1 X |
| 3,635,816 | 1/1972 | Golub .................................. 119/1 X |
| 3,654,903 | 4/1972 | Montgomery ........................ 119/15 |
| 3,814,057 | 6/1974 | Calvert et al. ........................ 119/15 |
| 4,187,946 | 2/1980 | Stevenson ........................ 119/15 X |

Primary Examiner—Hugh R. Chamblee
Attorney, Agent, or Firm—Laff, Whitesel & Rockman

[57] ABSTRACT

An integrated waste reclamation and processing system converts biodegradable liquid and solid waste into poultry products (or the like) and humus-like substances. The system uses earthworms and poultry in a manner in which biodegradable waste is first composted and then used as a substrate for newly hatched worms. The worms grow in the waste for about eighty days and then are harvested and fed to chickens or laying hens, in combination with other food. The waste left behind by the worms has humus-like properties which can be used as a soil conditioner on eroded, strip-mined, or desert land. This conversion system, which is preferably contained in a closed building and maintained operational throughout the year, it is applicable to the needs of small and large waste-producing institutions and facilitates the reclamation of biodegradable waste in a manner which is environmentally acceptable and economically feasible. The structures and machinery used in the system are also shown and described.

24 Claims, 11 Drawing Figures

MEANS AND METHODS OF RECLAIMING AND PROCESSING BIODEGRADABLE WASTE INTO POULTRY PRODUCTS AND HUMUS-LIKE SUBSTANCES

This invention relates to an integrated waste reclamation system and more particularly to means for and methods of naturally converting biodegradable waste into poultry products, humus-like substances and perhaps methane gas.

Environmental pollution and loss of non-renewable resources, which are so problematic in the industrialized nations, are mainly caused by a lack of adequate biodegradable waste reclamation systems. Most of the systems available at the present time are based upon use of microorganisms. The product which is usually recovered, called single cell protein (S.C.P), often finds application as protein supplement in animal feeds. Although technically feasible, such systems have found only a limited application, since they are often designed to handle only one type of waste and usually require large investments in machinery and energy. A large portion of the materials in the solid waste stream of municipal refuse is potentially recoverable. However, because of the low marketability and high cost of treating the biodegradable fraction, complete waste reclamation systems, which would make possible the recovery of valuable elements from municipal refuse, have found limited application.

Another problem posed by biodegradable waste is that it is often produced in quantities which are not large enough to justify an acquisition of a waste processing system by a single institution.

Biodegradable waste produced by different institutions has different characteristics in terms of contents and physical properties. At the present time, there are no economically feasible systems which enable a transformation of biodegradable waste into a food source for animals. Therefore, there is a need for a biodegradable waste reclamation system capable of meeting the needs of any waste producing institution.

Accordingly, an object of the invention is to provide new and improved biodegradable waste disposal and reclamation systems. Here, an object is to provide such reclamation systems which may fit the needs of different size units.

A further object of the invention is to provide natural means for and methods of reclaiming biodegradable waste.

Yet another object is to provide natural by-products, such as humus-like material, fuel, animal feed, and the like.

The integrated waste conversion system resulting from this invention is based upon findings that large quantities of earthworms (such as *Lumbricus rubellus* and *Eisenia foetida*, for example) can be raised on composted biodegradable waste. The nutritional value of the worms is such that a mixture of live or dried worms, corn and vitamins can be used as a substitute for commercial chicken or other feeds. Feeding trials have repeatedly shown that chickens and laying hens fed on worms, corn and vitamins perform as well as, or better than, their respective control groups fed on commercial feed. Furthermore, chickens fed on a protein-free diet, worms and vitamins performed better than a control group fed on commercial feed. This proves conclusively that earthworm protein supplies sufficient quantities of all of the essential amino acids required by chickens and other animals.

Amino acid analyses of earthworms homogenate confirmed the findings obtained from the feeding trials. Worms, unlike comparable protein sources such as fish, soybeans and microorganisms (S.C.P.), can be fed to day-old chicks without any processing. Therefore the nutrient losses that occur during the ordinary feed processing operations are eliminated and the energy required by such process is saved.

Furthermore, the worms thrive on waste materials that are not suitable for domestic animal consumption and are commonly used as sanitary landfills or are incinerated and pyrolysed.

Plants are the only autotrophic organisms of significant importance in the human food chain. Once food becomes waste and nutrient molecules are lost or destroyed through inadequate waste disposal systems, they can only be reconstituted through the cultivation of plants. Most plantcrops are seasonal and require a high energy input in the form of fertilizer and gas for farm or transport machinery.

Unlike other high protein crops such as soybeans and fish, worms can be grown indoors throughout the year, with a very low energy input. The worms do not require light and most of the heat energy required by the system can be obtained from solar heat collectors or as a by-product of the composting process that biodegradable waste undergoes prior to being fed to the worms.

Therefore the advantages of this invention are that it:

1. fully exploits the earthworm's ability to grow on composted biodegradable waste;
2. fully exploits the nutritional value of earthworms for animals in general and chickens in particular;
3. provides an integrated biodegradable waste reclamation system which meets the needs of almost any waste producing institution;
4. provides an integrated biodegradable waste conversion system capable of operating continuously under any climatic condition and with a low energy input;
5. provides an integrated farming system capable of operating on a small land area;
6. provides an integrated farming system capable of deriving human food from waste materials in a manner that is environmentally acceptable and economically feasible;
7. provides a full array of systems ranging from units for small communities to fully automated systems for sprawling urban areas, husbandry operations, and food industry conglomerates.

In keeping with an aspect of the invention, a system for digestion or partial conversion of biodegradable waste material is followed by a processing of the converted material by earthworms. The system principally comprises an earthworm-poultry farm, in which biodegradable waste is first composted and then used as a substrate for newly-hatched earthworms, particularly redworms. The worms grow in the waste for about eighty days and then are harvested and fed (preferably live) to chickens or laying hens. The residue which is left behind by the worms has humus-like properties which can be used as a soil conditioner on eroded, stripmined, or desert land. This conversion system is preferably contained in a close building and maintained operational throughout the year. It is applicable to the needs of small and large waste-producing institutions and facilitates the reclamation of biodegradable waste in a manner that is environmentally acceptable and economically feasible.

Two embodiments of the invention are shown in the attached drawings wherein:

FIG. 1 schematically depicts an exemplary urban waste collection and reclamation system which may employ the invention;

FIG. 2 schematically shows a waste-processing system including digesters and a worm farm;

Figure 9:
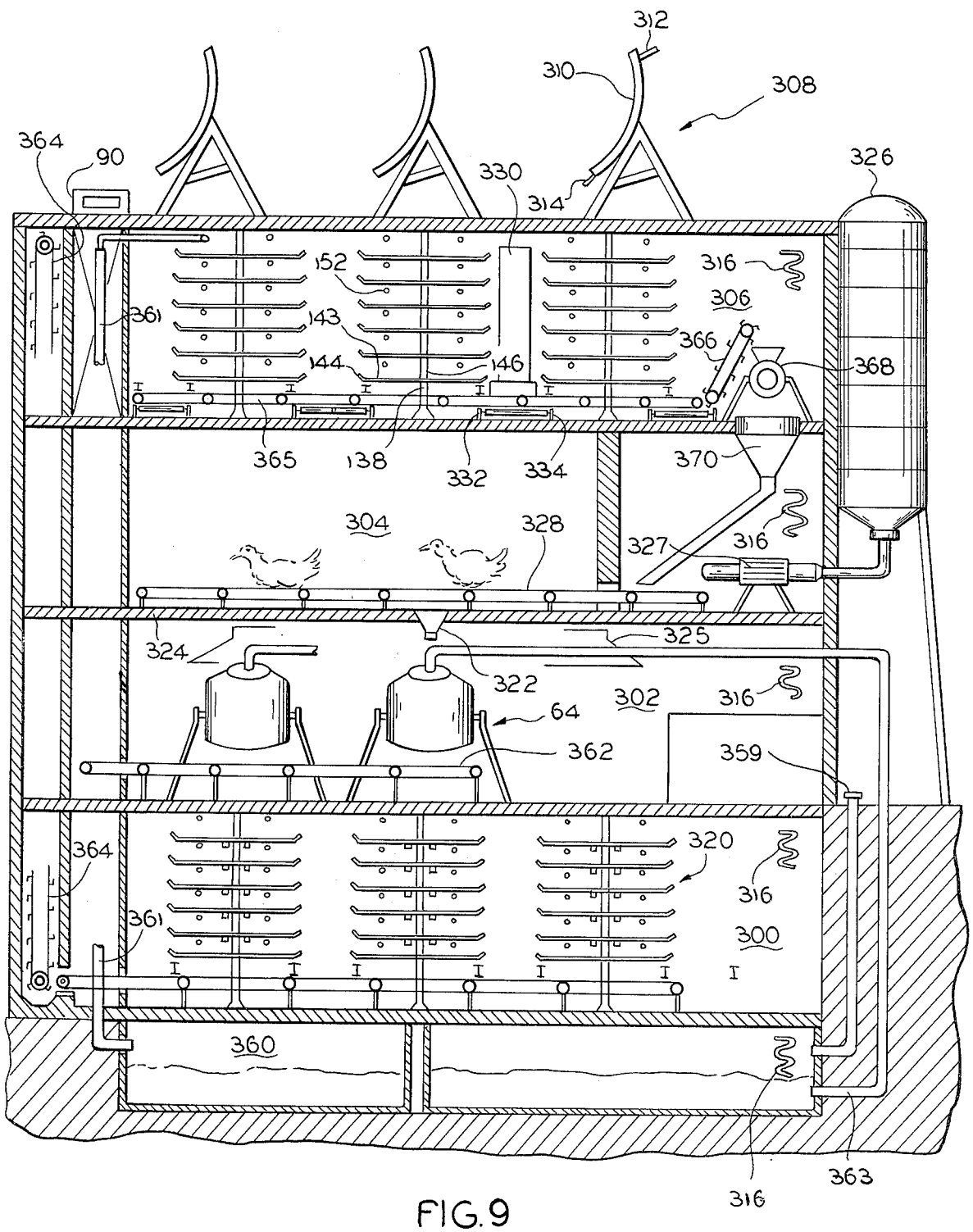
Figure 10:
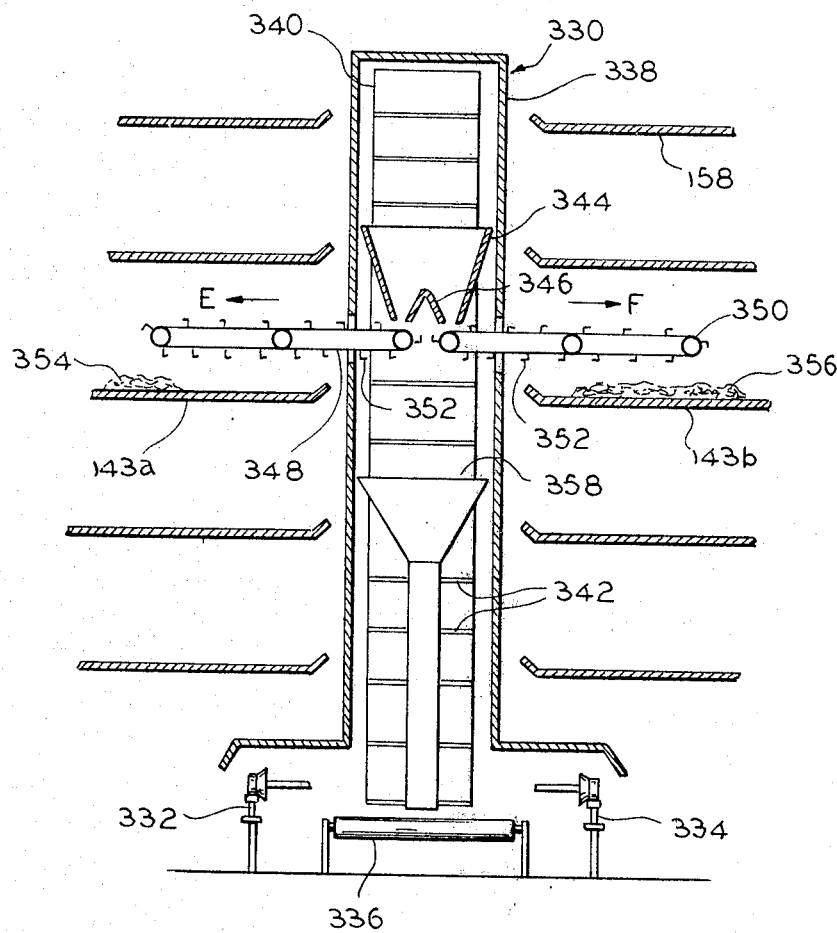
Figure 11:
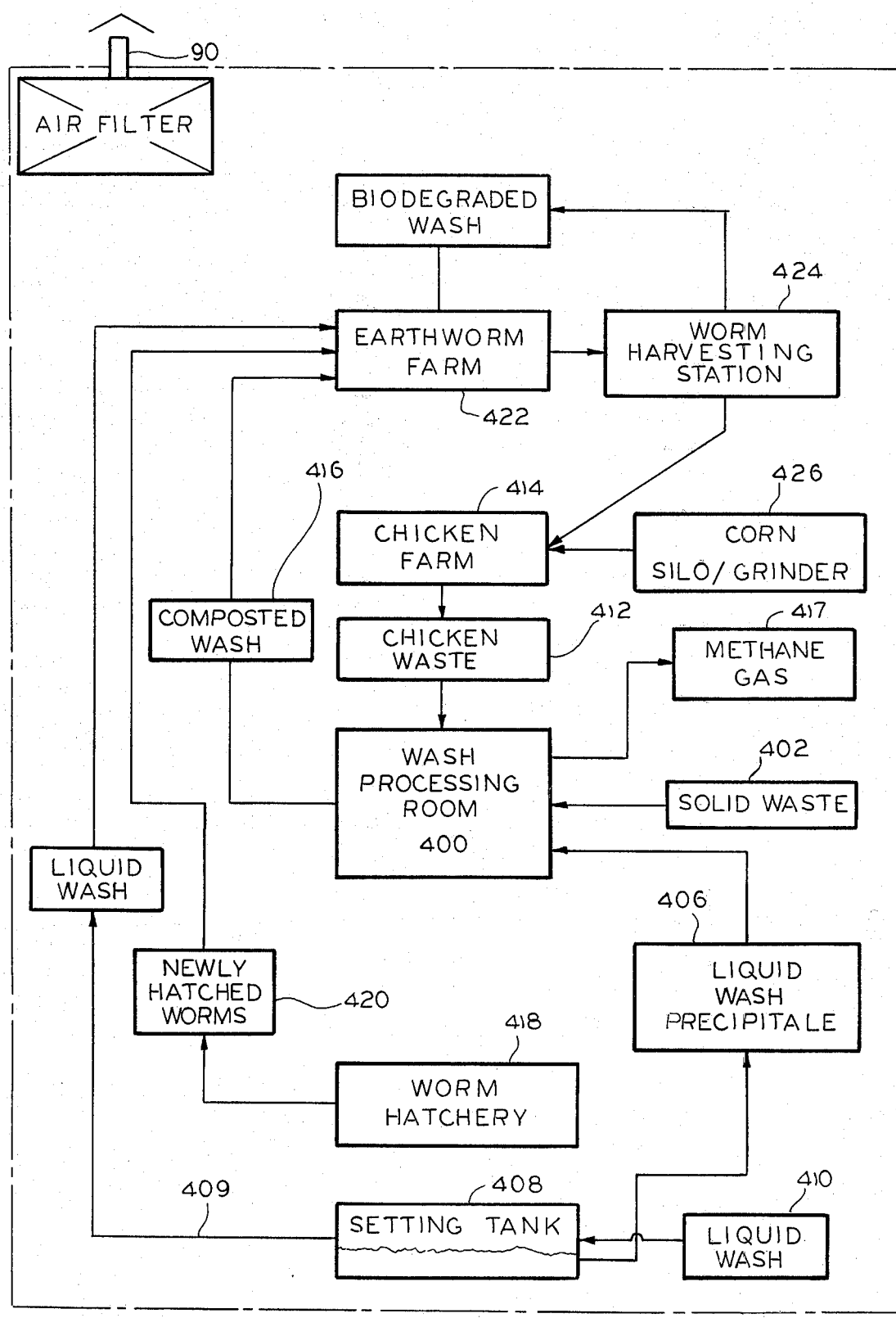

FIG. 9 schematically shows a preferred system in a high-rise configuration;

FIG. 10 shows an elevation of an alternative and preferred embodiment of a waste-spreading and worm-harvesting conveyor system; and FIG. 11 is a flow-chart diagram for explaining a process for practicing the invention.

Figure 1:
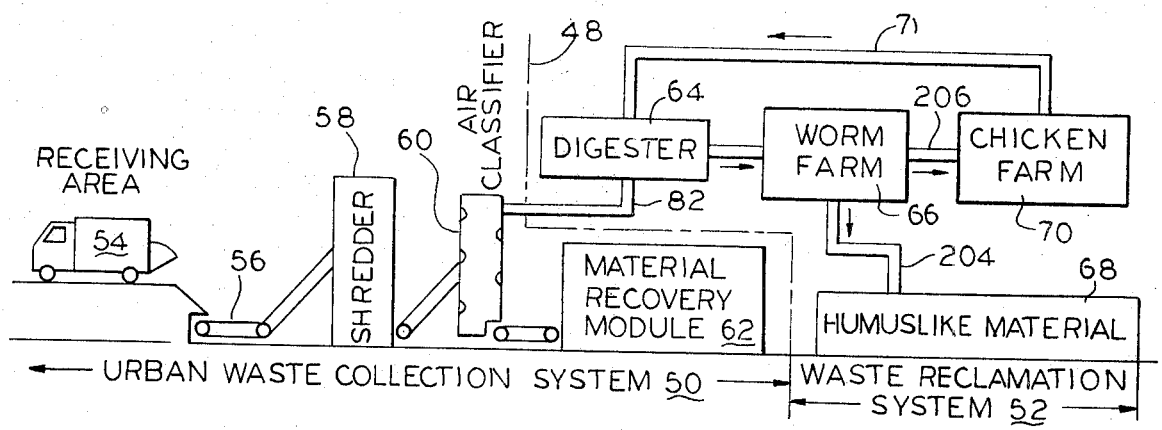

The system is depicted schematically in FIG. 1 as it might be used in connection with any convenient urban waste collection system. Depending on the availability of land, the system may be either contained in a high rise building or spread out horizontally. In either case the building may be equipped with solar heat collectors, and the system may be maintained operational throughout the year.

The system can absorb the biodegradable fraction of municipal refuse, sewage sludge (if it does not contain toxic levels of substances that cannot be biodegradable), neutralized or precipitated and leached agricultural waste such as animal manures, corn stover, sugar cane stalks, leaves and grass, etc., as well as liquid and solid waste from food processing plants. This system can be set up in a central location and absorb waste from several institutions at the same time.

FIG. 1 is divided by a dot-dashed line 48 with a more or less conventional urban waste collection system 50 shown on the left and the inventive reclamation system 52 shown on the right of line 48. The exemplary collection system usually involves a fleet of collection trucks 54 which dump their collected trash on a conveyor system 56 leading to a shredder or comminuting device 58, and trash classifier 60. The non-biodegradable material is deposited in a recovery module 62, for any conventional disposal. The biodegradable waste is fed into a digester 64 where it is fermented with bacterial action for a suitable period. After the digested or fermented material has passed its tests, it is conveyed to a worm farm 66 where it is fed to earthworms. When the worms have matured, and converted biodegradable waste into a humus-like material, they are then separated to be used as chicken feed and the humus-like material is removed at 68 for return to the earth for use in top soil. The separated worms are conveyed from the worm farm 66 to a chicken farm 70 where they are fed to chickens. Alternatively, the worms may be either heat- or freeze-dried and further processed into animal food.

Liquid waste is first stored temporarily in settling tanks, whereas solid waste is fed into comminuting equipment. The comminuted waste is then fed into a rotary drum digester. Liquid waste from the settling tanks or water is added to the waste in the drum in order to increase the moisture content up to 30% by wet weight. Particulate waste which precipitates from the solution in the settling tanks is removed from the tank by a suction device or bucket elevator system and fed into the digester. Subsequently the waste is tumbled for about half an hour in order to render the waste mixture as homogeneous as possible.

During digesting the content is tested for pH, carbon nitrogen ratio (C-N ratio), carbon phosphorus ratio (C-P ratio), potassium and for the presence of toxic levels of heavy metals, pesticides and the like. If necessary, balancing nutrients and moisture are added. Optimal conditions for speedy microbial waste degradation require a C-N ratio of about 20:10 and a C-P ratio of 100:1 with a moisture content of 50-60% by wet weight. If unwanted substances accidently find their way into the waste, attempts are made to neutralize, or precipitate and leach them. If the waste cannot be detoxified, it is either diluted with non-toxic waste or used for sanitary landfill.

The waste is subsequently composted for a period of ten days during which the pH and moisture of the waste are checked periodically and corrected if necessary. Optimal moisture content is 50-60% by wet weight. Throughout the composting period, the digester rotates slowly in order to aerate the waste. The temperature of the demposting waste is also monitored and kept above the thermal death point 70° C. (158° F.) of parasitic and patogenic organisms for at least two consecutive hours during two successive days. At the end of the composting process the waste is transferred by conveyor belt, bucket elevator and cart to the worm farm.

The waste from the chicken farm is returned at 71 to the digester 64. This waste may include any biodegradable material from the chicken farm which cannot be sold.

Figure 2:
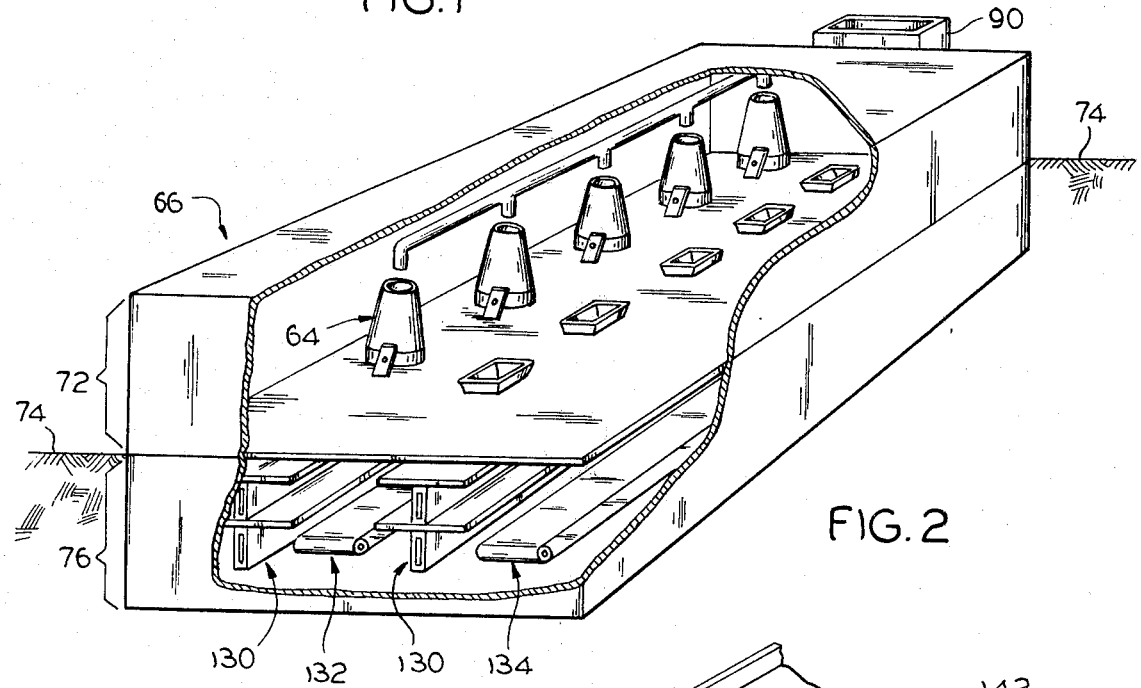

The general layout of one embodiment of a worm farm 66 is seen in FIG. 2. In general, this embodiment of the farm 66 is housed in two stories, preferably having one story 72 above the surface 74 of the earth and one story 76 being below the surface of the earth. The underground level 76 is preferred in this particular embodiment since the temperature, humidity, etc. are easily held at the natural embodiment and habitat of earthworms.

The first floor 72 contains a plurality of digesters 64 in which biodegradable waste is composted for about ten days. The number of digesters depends on the amount of the waste to be treated. Each digester may be designed to accomodate over fifty tons of waste. The digesters are preferably made of non-corrosive metal or laminated steel covered with non-corrosive plastic. The digesters are intended to operate aerobically but they are so designed that they can operate anaerobically, thus enabling the production of methane gas. In such case the digester is equipped with a cover which closes the digester hermetically. The cover is equipped with inlets and outlets through which buffer solution for regulating the pH of the waste is added and through which methane and carbon dioxide are pumped out of the digester. This characteristic feature of the digesters is of great importance in a time of dwindling energy resources.

The air in the digester room is filtered, sanitized, and deodorized at 90, before it is discharged into the atmosphere.

Figure 3:
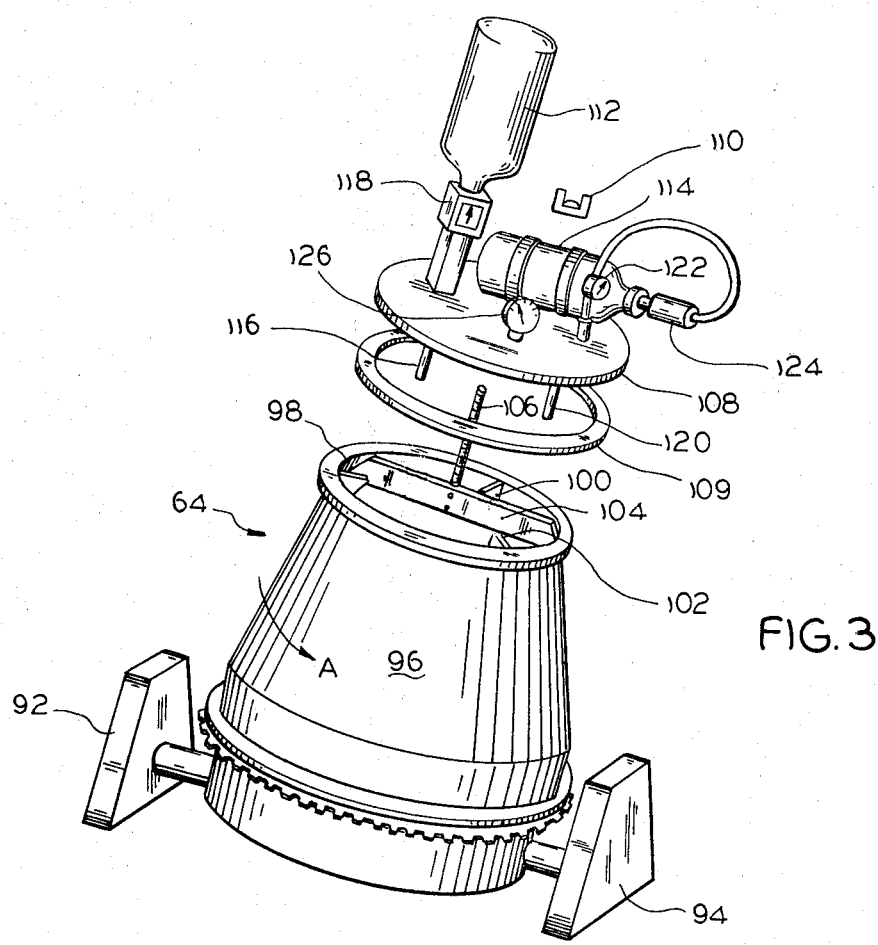
FIG. 3 shows mechanical details of an exemplary digester.

The details of an exemplary digester 64 are seen in FIG. 3. There are at least a pair of spaced parallel upright supports 92,94 with a tumbler drum 96 rotatably mounted between them. The interior of the tumbler drum 96 includes a plurality of blades 98,100,102 integrally attached to its inside surface. Preferably, the tumbler rotates at a slow speed such as 1 or 2 rpm, for example. Alternatively, the drum could rotate intermittently. More particularly, in one embodiment (FIG. 3), a suitable cross member 104 inside the tumbler drum 96 has an attached threaded rod 106 for fitting through a hole in top or disc 108 which seats itself on a gasket 109, positioned around the rim of the drum. A wing nut 110 is threaded on to rod 106 to seal the top onto the drum 96, in a gas-tight relationship. Mounted on the top 108, and turning with this particular drum 96, are two containers 112,114. The container 112 holds suitable acid-neutralizing chemicals (such as baking soda, for example) to control the pH factor of the fermenting material. A probe 116 extends from a standard pH meter 118 into the fermenting and digesting biodegradable material to control a dispensing of a suitable neutralizing chemical to hold a stable pH range (such as pH 6 to 8, for example). The pH factor is preferably 7.2.

A tube or pipe 120 extends from inside the tumbler drum 96, through the top 108, a pump 122 and $CO_2$ trap 124 to collect methane gas in the bottle 114. A pressure gauge 126 reads the internal pressure within the tumbler drum 96 to drive pump 122 for the gas collection system.

The lower floor 76 (FIG. 2) of the earthworm farm includes a plurality of open shelf units 130 on which the partially digested biodegradable waste may be spread and the worms may grow. Adjacent the shelf units 130 are conveyor systems 132,134 which distribute the waste and infant worms and later collect the mature worms and humus-like material from the shelves 130, during a harvesting operation. For convenience of description only this distribution system is shown as two conveyor belts, but other systems (e.g. lift trucks) may be used to reduce energy consumption.

The shelf units 130 are preferably constructed by assembling standard modules 135 (FIG. 4) which may be arranged in any convenient array. Each module includes a central upright section 138 which terminates at the module bottom in a connector configuration 140 that sets upon and is supported by a mating connector 142 at the module top. Thus, any convenient number of these modules may be stacked vertically and also any convenient number of modules may be placed end to end.

Each module has a pair of opposing shelves 143 which extend outwardly on opposite sides of the center support 138. The outer edge of each shelf is turned up, as at 144, to receive and retain a mixture of biodegradable waste and infant worm culture.

Conveniently, each shelf unit module (FIG. 4) may be made of cast cement or plastic. A channel or hollow passageway 146 is formed longitudinally throughout the length of the central section 138. A series of windows 148 communicate into the hollow passageway 146. This way, air pumped though the passageway 146 spreads out through the windows 148, over, under and around the shelves.

Figure 4:
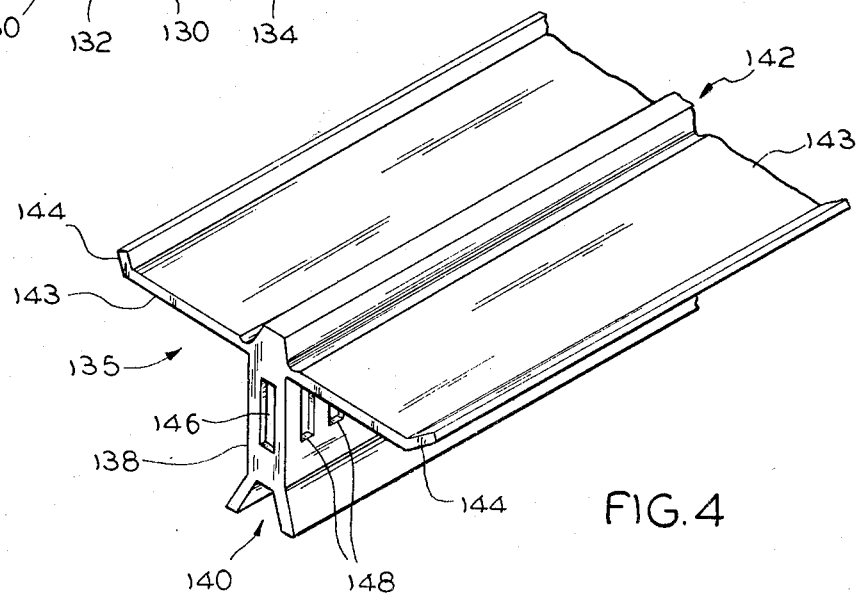
FIG. 4 shows a single module of a shelf-like structure used to build an earthworm farm.
Figure 5:
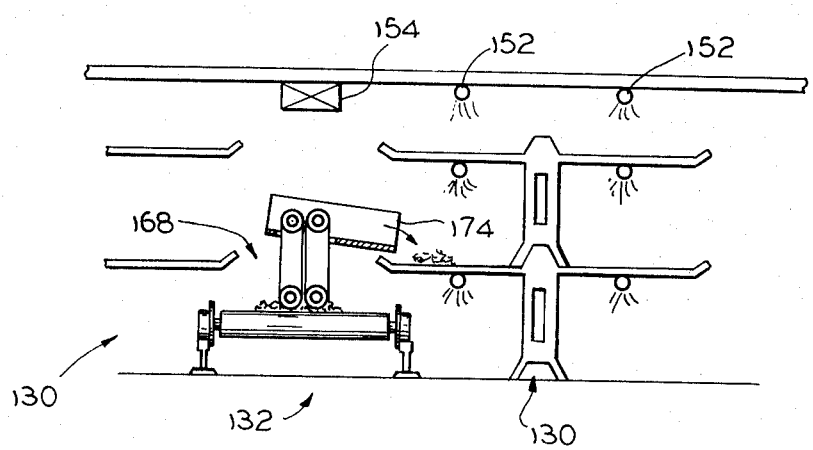
FIG. 5 shows an assembly of a plurality of modules of FIG. 4 to form an earthworm farm.

FIG. 5 shows (by way of example) two rows of shelf units 130,130 constructed from four modules of FIG. 4, stacked one on the other and placed in a side-by-side, spaced parallel relationship. The plane of FIG. 5 is such that the length of the shelving does not show. Nevertheless, the shelving may extend any convenient distance by placing additional modules behind those seen in this figure. Likewise, any convenient number of shelf modules may be placed side by side.

Above each shelf, there is a sprinkler system 152 which may keep the shelves moist. Suitable additives may also be placed in the water that is sprayed by the sprinkler system 152. These additives may include nutrients, antibiotics or other suitable medicinal remedies. This quick application of medicines may be extremely important if an epidemic disease should begin to spread throughout the worm culture.

Normally, the room containing the shelves is kept in total darkness so that the worms will be in their normal underground habitat.

Figure 6:
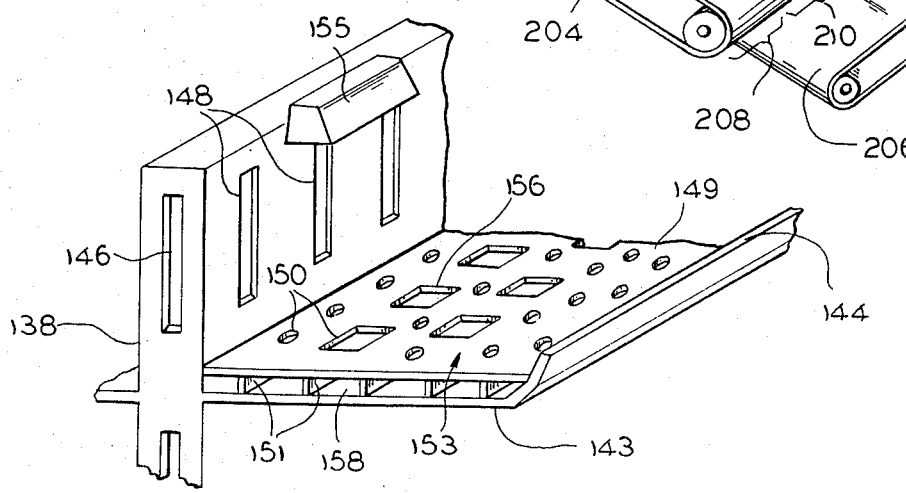
FIG. 6 shows part of a module similar to the module of FIG. 4, which is used for breeding earthworms.

The worms are bred in a hatchery which is preferably located underground, where temperature and moisture can be easily controlled throughout the year with a very low energy input. The hatchery uses a module (FIG. 6), which is similar to the module of FIG. 4, equipped with the shelves on which a selected breeding stock of earthworms or, particularly, redworms breeds continuously. Any suitable frame work 153 is placed over the shelves to adapt them to use as a hatchery. This frame includes a floor 149 having holes 150, 156 formed therein. The floor is supported in an elevated position by a plurality of longitudinal members 151 which form spaces 158 under the floor and above the shelves. The biodegradable material, seeded with the breeding stock of earth worms, as piled on top of the floor.

Approximately, once every two weeks, a bright light is directed from source 155 onto the bedding and the breeding stock of worms migrate through holes 150 156 and into dark recesses 158 under the floor 149. Then, the bedding containing worm eggs is removed and incubated for about fifteen days. Subsequently, the newly hatched worms are seeded onto the composted waste on shelves 130 where they grow and are ultimately fed to chickens and laying hens.

Any suitable machinery may be used for loading and unloading the breeding shelves with bedding and worm eggs similar to that used to deposit waste and collect worms and the humus-like material. Peat moss, shreaded paper, sawdust, etc. can be used as bedding. The breeder worms will migrate back into the bedding when the lights are turned out.

Figure 7:
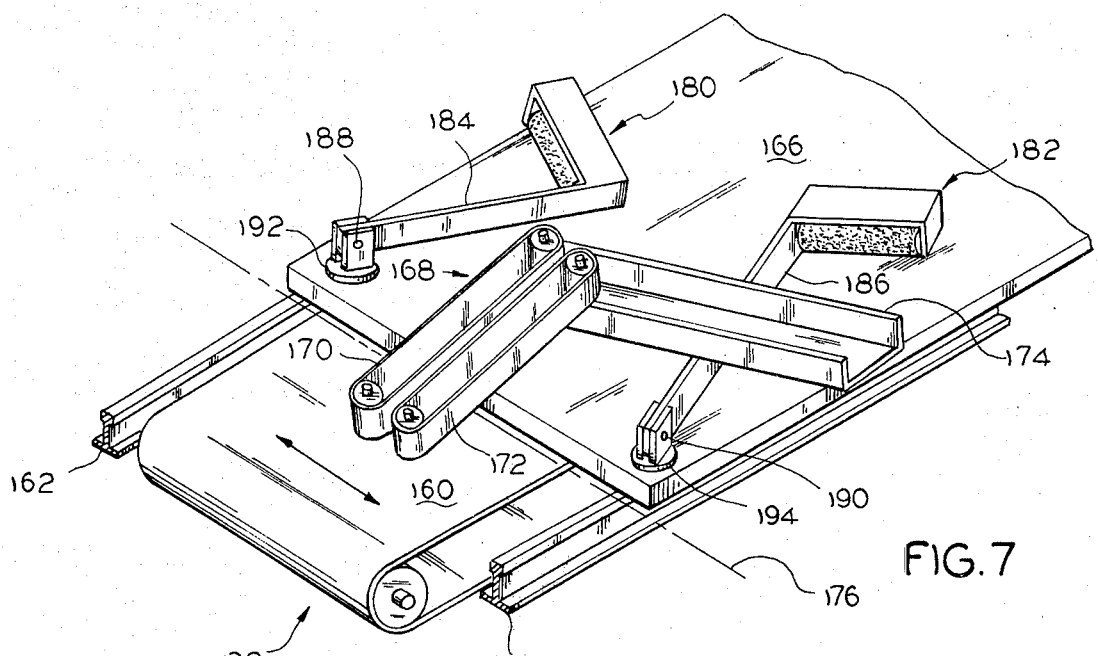
FIG. 7 shows a system for depositing partially digested waste material on the worm farm structure of FIG. 5 and for harvesting the mature worms and humus-like material therefrom.

Rails 162,164 (FIG. 7) are positioned on opposite sides of any suitable distribution means. Here again, for purposes of this description only, the distribution means is shown as a conveyor belt. In actual practice the energy required to run a conveyor belt system may become excessive. Therefore, any other more energy efficient means may be used.

A platform 166 is mounted on wheels (not shown) which ride on the rails 162,164. Therefore, the platform 166 may travel back and forth throughout the length of the shelving. Mounted on the platform 166 is an elevator system 168. Here a pair of conveyor belts 170,172 are supported in a vertical face-to-face relationship, which discharges biodegradable waste material from belt 160 or another suitable means onto any selected shelf. A suitable chute 174 is positioned under the output end of the elevator to deposit biodegradable waste material onto an adjacent shelf.

In operation, the platform 166 travels over rails 162,164, from one end of the shelves to the other end, while biodegradable waste material is picked up and deposited on the shelves. In addition, to the biodegradable waste material, a mixture of baby earthworms, in a suitable bedding, is also deposited, so that a certain number of baby worms are seeded into every unit amount of biodegradable waste material.

After the earthworms and biodegradable material have been on the shelves for a sufficiently long period of time, all biodegradable waste has been consumed by the earthworms and the only remaining material is a rich humus-like material.

The harvesting of the humus-like material and earthworms is carried out by the same material handling system 132 (FIG. 7) that is originally used to lay down the biodegradable waste. More particularly, the elevator belts 168 (FIG. 7) may be tilted around axis 176 and laid down flat on the platform 166. Then a pair of brushes and hoppers 180,182 which are mounted on the ends of arms 184,186 pivot upwardly on axes 188,190 and swivel outwardly on bearings 192,194 to support the brushes over the shelves and bring the material on the shelves inwardly toward the conveyor belt 160 or other suitable material handling or transport means.

Figure 8:
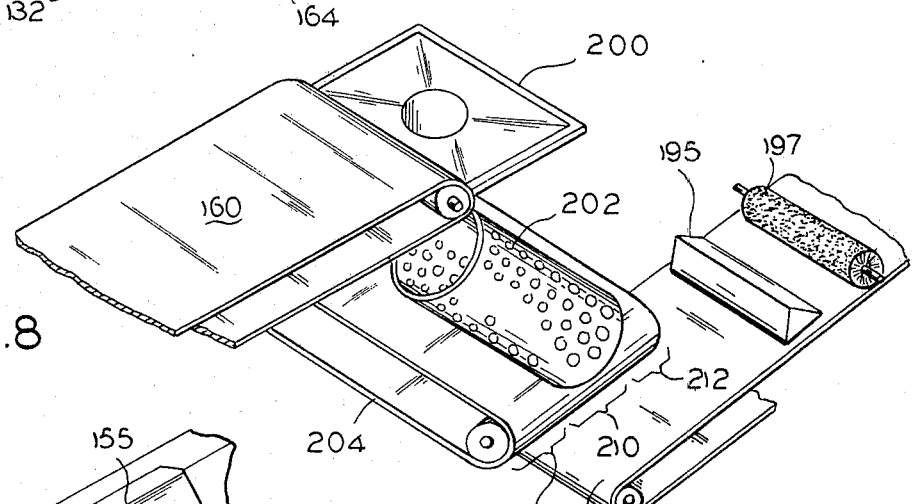
FIG. 8 is a schematic, perspective view of a worm and humus-like material separator.

The worms are separated from the harvested material by passing it through an inclined tumbling cylinder 202 (FIG. 8) which has walls perforated with holes of different diameters, small holes at the beginning and large holes at the end. Most of the waste sieves through the cylinder holes.

The worms and some waste are recovered at the end of the cylinder and can be further cleansed by exposing such worm-waste mixture to a bright light from source 195. In the presence of such light, the worms clump together and push all the waste to the outside where it can be easily brushed away at 197 before the worms are delivered to the chicken farm. The harvesting station may also equipped with a hot water bath where the worms can be pasteurized before being fed to the chickens, if disease appears.

In greater detail, the conveyor belt 160 dumps the sweepings into a funnel-shaped guide 200 (FIG. 8) which directs them into an angularly mounted tumbler drum 202 so that the sweepings fall downwardly with respect to the vertical. Thus, the sweepings are deposited from the funnel 200 into the drum 202.

The drum 202, positioned over any suitable transport means (here represented as a pair of conveyor belts 204,206,), is generally cylindrical with walls pierced by graduated size holes increasing in diameter from very small holes at the top to relatively large holes at the bottom. Thus, dust and small particles of humus-like material tend to rain down in a first area 208, medium-size balls of humus-like material tend to rain down in a second area 210 and larger clods tend to fall in area 212. Transport means 204 is also shown in FIG. 1 as connecting the output of the earthworm farm 66 with a humus-like material collector 68.

Earthworms do not tend to fall through the holes in the wall of drum 202. Instead, almost all of them tend to fall out the end of the drum and onto a worm collection station, here shown as conveyor 206. These worms are then conveyed to a chicken farm 70 (as also shown in FIG. 1).

The general layout of a second and preferred embodiment of the system is shown in FIG. 9. This particular setting is a high rise unit primarily intended for communities or locations in which land is scarce or otherwise limited. The buildings are preferably equipped with solar heat collectors, especially for maintaining environmental conditions.

In greater detail, the building of FIG. 9 shows the earthworm hatchery at 300, composters room at 302, chicken farm at 304, earthworm farm at 306, and solar collectors at 308. The solar collectors are preferably double-walled parabolic reflectors, as at 310, having inlet and outlet pipes 312,314, such as copper tubing, for conveying water. Alternatively, copper tubing may be positioned in any convenient location to be heated by solar energy falling on the reflectors. These pipes 312,314 lead to heating coils 316 which may be placed around the building in any suitable locations. The water heated by the solar reflectors may be conveyed to heat any of these coils and to warm any area where heat is required.

The chicken farm 304 is preferably located on a floor above the digesters in room 302. The chicken farm can be either an open floor or a cage operation. The waste produced by the chickens is swept through one or more holes 322 in the floor 324, fed into the digesters, and composted together with exogenous waste. Another advantage realized by placing the chicken farm above the digesters is that much heat is generated by the biogradable waste material during the digestion process. Since chickens need to be warm, the heat rising from the digesters provides both a reliable and a low-cost heat source. A hook 325 is positioned over the digesters to collect such heat.

A silo 326 containing corn and a grinder 327 for milling corn are also located to deliver cracked corn onto a chicken feeding conveyor 328 which also delivers the worms to the chickens. If required, vitamins and medicines are supplied through the drinking water.

Although worms can be fed to different types of poultry, or other animals, the chicken strains available at the present time are the most efficient converters of crude protein and energy into products which are edible by humans. Therefore, there is presently a maximum efficiency growing out of the combination of earthworms and chickens, as taught by this system.

The room or rooms 306 above the chicken farm are occupied by the worm farm, which is equipped with the same type of shelves that are shown in FIG. 4 and arranged in any convenient array.

In the embodiment of FIG. 9, a transport system of belts stretches around the worm farm and the worm hatchery. Again, conveyor belts are shown by way of example; however, other more energy efficient distribution systems may be used. In front of each row of shelves, there is a loader-harvester device 330 which moves on rails 332 to load and unload the waste on each row of shelves.

The details of the loader-harvester device 330 are shown in FIG. 10. This device 330 comprises a number of wheels which ride on rails 332 on opposite sides of a conveyor belt 336. Waste is conveyed from a common belt running throughout the worm farm to the belts 336 which are individually associated with the rows of shelves. The housing 338 of the device 330 extends vertically upwardly from the rails 332. A vertically oriented conveyor belt 340 is mounted within housing 338, carries integral transverse members 342 which project therefrom. Those transverse members act as an endless chain of buckets for picking up and carrying the waste upwardly and over the top of the belt to a point where it falls, under gravity, into a hopper 344.

Waste falling into the hopper 344 is divided by a member 346 onto two oppositely disposed horizontal conveyor belts 348,350, each of which has integral transverse members 352 for laterally conveying the waste in directions E,F, and depositing it on the shelves 143. The deposited waste 354,356 contains both biodegradable material and infant earthworms. This assembly may be raised or lowered to deposit the waste and infant worms on any shelf in the array of the shelves.

If the belts 340,348,350 are run in one direction, the waste is picked up from conveyor belt 336 and deposited on selected ones of the shelves 143. If the belts are run in an opposite direction, the transverse members 352 sweep the mature worms and humus-like material from the shelves 143 and back to the conveyors 340,336,332. A hopper 358 catches the mature worm mixture and directs it toward the conveyor belt 336.

The same type of machinery is used in the hatchery 300 (FIG. 9) for seeding newly hatched worms into the waste and for removing the bedding and earthworm eggs.

The various conveyors are distributed throughout the worm farm 306 in such a manner that it forms an endless loop. Therefore, any material which either is not picked up from or falls back onto the conveyor merely circles around to another point where it may be picked up.

The waste-processing system of FIG. 9 operates in the following manner. The waste collection system of FIG. 1, or any other suitable system, deposits solid wastes in digesters 64 and liquid wastes (via pipe 359) in a settling tank 360. There, the liquid waste settles so that liquid may be pumped up pipe 361 to the sprinkler system and the settled sludge may be pumped out pipe 363. Anything solid which is biodegradable is pumped into the digesters where it goes through a digestion or fermentation process. After a suitable fermentation period, the digesters dump waste into a suitable transportation means (such as conveyor 362) leading to a bucket elevator 364.

This waste is carried by bucket elevator shaft 364 which may be driven in one direction to deliver the waste to the worm hatchery 300 and in an opposite direction to deliver both the worm eggs and the waste to the worm farm 306.

The conveyors 364,365 deliver the biodegradable waste to the worm farm, while conveyors 330,365, and a bucket elevator 366 deliver mature worms and humus-like material to the earthworm separator 368 (similar to FIG. 8) which separates the worms and deposits them in a hopper 370. If desired, this hopper may also include pasteurizing elements which heat the worms to a prescribed temperature (about 70° C. or 160° F.) for a predetermined period of time sterilize the worms and kill the bacteria or other harmful organism. The output of the worm separator or collector is deposited from hopper 370 onto conveyor 328 along with corn from silo 326.

FIG. 10 is a flow diagram which shows the steps in the inventive process, which have been described above.

Comminuted biodegradable waste is fed through size reduction equipment where it is shredded, ground, or otherwise placed in a conveniently handled condition, and fed into a composter or digester, all represented by a block marked waste processing room 400. In addition to the comminuted biodegradable waste material, any other suitable biodegradable material may also be processed. This other material being represented as solid waste 402 or liquid waste precipitate 406, taken from the bottom of a settling tank 408. The liquid from the settling tank 408 is delivered at 409 directly to the earthworm farm 422, preferably through the sprinkler system. The source of the liquid waste, represented at 410, might be runoff of a food-processing plant, for example. Also, the return from the chicken farm 414 to the waste processing room 400 may be deposited via 412 and into the biodegradable material.

After a suitable digestion period, the composed biodegradable waste is fed through a leaching and fortifying station 416, where toxicants are washed out or neutralized. If the biodegradable waste lacks basic nutrients which are required by the earthworms, they may be here added to fortify the material. From station 416, the biodegradable waste is transported to the earthworm farm 422. Infant worms are transported from the hatchery 418 through a distribution means 420 to the earthworm farm 422. Methane gas may be extracted at 417. From there, the humus-like material is separated at 424 to be used as a soil conditioner. The mature earthworms separated at 424 are fed into chicken farm 414, along with corn from grinder 426.

This waste conversion system is carefully designed for the control of any adventitious parasites or pathogens that may enter the system because:

1. the composting process heats the waste to a temperature which is well above the thermal death point of parasitic and pathogenic organisms;

2. the breeding stock of worms is carefully analyzed for pathogenic and parasitic organisms before it is introduced and used in the system hatchery;

3. the sprinkler system can be used to spray the waste material with antibiotics and other types of medication which may be appropriate to the process;

The system can absorb the biodegradable fraction of municipal refuse as well as sewage sludge if it does not contain toxic levels of substances that cannot be biodegraded, leached or precipitated.

The system can also accept animal manures, composted biomass (corn stover, sugar cane stalk and leaves, grass, etc.) as well as liquid and solid waste from food-processing plants.

Although the presence of the chicken farm in this system makes the recycling operation highly efficient, the room 304 occupied by the chicken farm may also be equipped with a freeze-dry apparatus so that the worms can be dried, ground up, stored in the silo and, subsequently, transported elsewhere and used in the manufacture of animal feeds.

The biodegraded waste left behind after the worms are harvested has humus-like properties and is intended to be used as soil conditioner on eroded, strip-mined, desert, or normal agricultural land.

Those who are skilled in the art will readily perceive how to modify the system. Therefore, the appended claims are to be construed to cover all equivalent structures which fall within the true scope and spirit of the invention.

I claim:

1. An integrated waste process for the conversion of biodegradable waste into animal products and humus-like substances, said process comprising:

a. partially digesting biodegradable waste over an extended period of time in a controlled environment;
b. spreading a mixture of said partially digested biodegradable waste and earthworms for a period of time which is long enough for said earthworms to grow to optimal size;
c. collecting said spread mixture;
d. separating said earthworms from said humus-like material;
e. feeding said earthworms to animals; and
f. harvesting food and by-products of said animals for human consumption.

2. The process of claim 1 wherein step (a) includes the added step of fragmenting and homogenizing said biodegradable waste prior to said digesting.

3. The process of claim 1 and the added step of feeding back waste material from said animals to the partial digestion of step (a).

4. The process of claim 1 and the added step of preparing said waste for speedy microbiological degradation.

5. The process of claim 4 and the added steps of testing said partially digested waste of step (a) for nutrients and toxicants, leaching or neutralizing unwanted components from said partially digested waste.

6. The process of claim 1 wherein step (b) comprises the added step of automatically conveying said biodegradable waste material to a series of shelves.

7. The process of claim 1 wherein step (c) includes the added step of automatically collecting humus-like material and worms from said spread mixture.

8. An integrated waste processing system for the conversion of biodegradable waste into animal products and humus-like material, said integrated material comprising:
a. means for comminuting said waste material;
b. means for at least partially digesting the material prepared by means (a);
c. means for spreading said material digested by means (b), seeded with earthworms;
d. means for collecting the spread material and earthworms;
e. means for separating the earthworms from the collected material;
f. means for feeding the separated earthworms to animals; and
g. means for collecting a humus-like material separated from said earthworms.

9. The system of claim 8 and means associated with means (b) and (c) for maintaining a balanced nutriment to said material.

10. The system of claim 8 wherein the means of clause (a) comprises drum means rotatably mounted for at least partially digesting biodegradable waste material, means mounted on and rotating with said drum means for maintaining the pH of said tumbling biodegradable waste material within a predetermined pH range, means also mounted on and rotating with said drum means for collecting methane gas, and means responsive to pressure buildup within said drum for pumping said gas into said gas-collecting means.

11. The system of claim 8 wherein the means of clause (c) comprises a plurality of stacked shelves arranged in a spaced parallel relationship, means extending parallel to and in the space between said shelves for depositing biodegradable material on and collecting said biodegradable material from said shelves, and means for controlling the moisture content of said material while it is on said shelves.

12. The system of claim 8 and means for ventilating said spread material to maintain fresh air over and around said material.

13. The system of claim 8 and means including said moisture content control means for supplying a fluid in controlled amounts to said spread material.

14. The system of claim 8 wherein said collector means comprises conveyor means mounted on rails extending longitudinally adjacent said spread material and means including a platform mounted on said rails for movement over and along the rails, for picking up and distributing said spread material.

15. The system of claim 14 wherein said collecting means further comprise means on said platform means for sweeping up said material, and means for guiding and directing the sweepings onto a material collection device.

16. The system of claim 15 wherein said collecting means further collects the humus-like material and worms, and said means for separating said humus-like material from said worms comprising a rotary drum having a wall pierced by holes of different diameters, said holes beginning at the top of the drum with small diameter holes and graduating in size to large diameter holes at the bottom of the drum, and means for rotating said drum about an axis which is inclined with respect to the vertical.

17. The system of claim 8 and means for normally darkening said spread material;
a. means for shining bright light onto said darkened material to drive said earthworms into dark areas; and
b. means for collecting said spread material from said lighted area.

18. The system of claim 17 and means for exposing said material collected from said lighted area to earthworm incubation conditions for a predetermined period of time.

19. The system of claim 18 and means for spreading said incubated material in an area where a biodegradable waste material is also spread.

20. The system of claim 19 and means for collecting the spread incubated and waste material and means for tumbling said collected material to separate the worms from the humus-like material.

21. The system of claim 20 and means for exposing said tumbled material to light in order to cause said earthworms to clump together and push said humus-like material away from them, and means for sweeping the pushed-away material from said worms.

22. The system of claim 20 and means for pasteurizing the separated worms.

23. An integrated biodegradable waste disposal system and chicken farm comprising means for converting biodegradable waste material over an extended period in a controlled environment to produce a partially digested mass, said waste material including some solid materials, combining said partially digested mass after said extended period with at least some earthworms and means for spreading said combination in a dark environment for an extended period of time, means for collecting and separating said earthworms from said spread mass, and means for feeding said separated earthworms to chickens.

24. The farm of claim 23 and means for feeding a corn material to said chickens along with said separated earthworms.

* * * * *

UNITED STATES PATENT AND TRADEMARK OFFICE
CERTIFICATE OF CORRECTION

PATENT NO. : 4,262,633

DATED : April 21, 1981

INVENTOR(S) : Leandro Taboga

It is certified that error appears in the above—identified patent and that said Letters Patent is hereby corrected as shown below:

Column 4, line 51, "embodiment should be -- environment --.

Signed and Sealed this

Fifteenth Day of September 1981

[SEAL]

Attest:

Attesting Officer

GERALD J. MOSSINGHOFF

Commissioner of Patents and Trademarks